United States Patent
Kim et al.

(10) Patent No.: US 10,448,925 B2
(45) Date of Patent: Oct. 22, 2019

(54) ULTRASONIC DIAGNOSTIC APPARATUS AND METHOD FOR REDUCING CLUTTER

(71) Applicant: SAMSUNG MEDISON CO., LTD., Hongcheon-gun (KR)

(72) Inventors: Deok-gon Kim, Hongcheon-gun (KR); Moo-ho Bae, Hongcheon-gun (KR); Sung-bae Park, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 548 days.

(21) Appl. No.: 14/771,272

(22) PCT Filed: Feb. 28, 2014

(86) PCT No.: PCT/KR2014/001685
§ 371 (c)(1),
(2) Date: Dec. 9, 2015

(87) PCT Pub. No.: WO2014/133360
PCT Pub. Date: Sep. 4, 2014

(65) Prior Publication Data
US 2016/0113625 A1    Apr. 28, 2016

(30) Foreign Application Priority Data
Feb. 28, 2013 (KR) .................. 10-2013-0022374

(51) Int. Cl.
*A61B 8/00* (2006.01)
*G01N 29/22* (2006.01)
(Continued)

(52) U.S. Cl.
CPC ............ *A61B 8/4494* (2013.01); *A61B 8/145* (2013.01); *G01N 29/221* (2013.01);
(Continued)

(58) Field of Classification Search
CPC ......... A61B 8/00; A61B 8/145; A61B 8/4494; G01N 29/221; G01N 29/262;
(Continued)

(56) References Cited

U.S. PATENT DOCUMENTS 6,551,246 B1    4/2003  Ustuner et al.
6,685,641 B2    2/2004  Liu
(Continued)

FOREIGN PATENT DOCUMENTS

EP      2 101 191 A2       9/2009
KR      10-2009-0058447 A  6/2009
(Continued)

OTHER PUBLICATIONS

Communication dated Sep. 15, 2016 issued by the European Patent Office in counterpart European Patent Application No. 14756441.3.
(Continued)

*Primary Examiner* — Amelie R Gillman
(74) *Attorney, Agent, or Firm* — Sughrue Mion, PLLC

(57) ABSTRACT

An ultrasonic diagnostic apparatus and an ultrasonic diagnostic method are provided. The ultrasonic diagnostic apparatus includes: a transducer for performing interconversion between an acoustic wave and an electric signal; and a transmitter for controlling the transducer so as to allow a plurality of plane waves to be transmitted through a plurality of sub-apertures.

7 Claims, 6 Drawing Sheets

(51) Int. Cl.
*G01N 29/26* (2006.01)
*G01N 29/34* (2006.01)
*G01S 7/52* (2006.01)
*G01S 15/89* (2006.01)
*A61B 8/14* (2006.01)

(52) U.S. Cl.
CPC ......... *G01N 29/262* (2013.01); *G01N 29/343* (2013.01); *G01S 7/52077* (2013.01); *G01S 7/52085* (2013.01); *G01S 15/8927* (2013.01); *A61B 8/00* (2013.01)

(58) Field of Classification Search
CPC .............. G01N 29/343; G01S 15/8927; G01S 7/52077; G01S 7/52085
See application file for complete search history.

(56) References Cited

U.S. PATENT DOCUMENTS

| | | | |
|---|---|---|---|
| 8,133,182 B2 | 3/2012 | Wagner | |
| 2002/0093880 A1* | 7/2002 | Nakamura | G01S 7/52003 367/88 |
| 2003/0139664 A1* | 7/2003 | Hunt | A61B 8/00 600/407 |
| 2004/0034305 A1 | 2/2004 | Song et al. | |
| 2007/0043295 A1* | 2/2007 | Chomas | A61B 8/481 600/458 |
| 2007/0167752 A1* | 7/2007 | Proulx | G01S 7/52095 600/437 |
| 2008/0114253 A1 | 5/2008 | Randall et al. | |
| 2008/0119735 A1* | 5/2008 | Lin | A61B 8/00 600/450 |
| 2009/0141957 A1 | 6/2009 | Yen et al. | |
| 2009/0234230 A1* | 9/2009 | Bercoff | G01S 7/52049 600/447 |
| 2010/0099986 A1 | 4/2010 | Azuma et al. | |
| 2010/0280373 A1 | 11/2010 | Fan et al. | |
| 2011/0141052 A1 | 6/2011 | Bernstein et al. | |
| 2012/0232388 A1* | 9/2012 | Curra | A61B 8/466 600/438 |
| 2013/0148894 A1 | 6/2013 | Yamamoto et al. | |
| 2013/0218012 A1 | 8/2013 | Specht et al. | |

FOREIGN PATENT DOCUMENTS

| | | |
|---|---|---|
| KR | 10-2014-0129246 A | 11/2014 |
| WO | 2012029460 A1 | 3/2012 |

OTHER PUBLICATIONS

Jorgen A. Jensen, et al; "A New Method for Estimation of Velocity Vectors"; IEEE Transaction on Ultrasonics, Ferroelectric and Frequency Control; vol. 45; No. 3; May 1, 1998; XP011437757; pp. 837-851 (16 pgs. total).

International Search Report dated May 20, 2014 issued by International Searching Authority in counterpart International Application No. PCT/KR2014/001685.

Written Opinion dated May 20, 2014 issued by International Searching Authority in counterpart International Application No. PCT/KR2014/001685.

Bae et. al, "Clutter Reduction in Plane Wave Synthetic Aperture Imaging", Joint UFFC, EFTF, and PFM Symposium, 2013, 4 pages total, IEEE.

Communication dated Jan. 18, 2016, issued by the Korean Intellectual Property Office in counterpart Korean Application No. 10-2014-0024652.

Communication dated Oct. 12, 2018, from the European Patent Office in counterpart European Application No. 14756441.3.

* cited by examiner

ULTRASONIC DIAGNOSTIC APPARATUS AND METHOD FOR REDUCING CLUTTER

CROSS REFERENCE TO RELATED APPLICATIONS

This application is a National Stage of International Application No. PCT/KR2014/001685 filed Feb. 28, 2014, which claims priority to Korean Patent Application No. 10-2013-0022374 filed Feb. 28, 2013, the contents of all of which are incorporated herein by reference in their entireties.

TECHNICAL FIELD

The present invention relates to an ultrasonic diagnostic apparatus and method.

BACKGROUND ART

In general, ultrasonic diagnostic apparatuses transmit ultrasound waves to an object such as a human or animal and detect echo signals reflected from the object, thereby displaying a tomographic image of a tissue inside the object on a monitor and providing to information necessary for diagnosis of the object. By performing the above process, the ultrasonic diagnostic apparatuses have been used for medical purposes such as detecting foreign substances within a living organism, assessing injuries, monitoring a tumor, and observing a fetus.

Ultrasound may be classified mainly into focused ultrasound and plane-wave is ultrasound. Focused ultrasound has the advantage of providing high resolution imaging but requires a large number of transmissions. On the other hand, plane-wave ultrasound is advantageous in acquiring an ultrasound image of a large area with a relatively small number of transmissions. Furthermore, the use of plane-wave ultrasound allows relatively simple calculation of a focusing delay for focus synthesis.

However, an ultrasound image acquired using plane-wave ultrasound may show a higher clutter level than when using focused ultrasound. As the clutter level of an ultrasound image increases, the contrast resolution of the ultrasound image may be degraded.

DETAILED DESCRIPTION OF THE INVENTION

Technical Problem

The present invention provides an ultrasonic diagnostic apparatus and method of reducing a clutter level.

Technical Solution

According to an aspect of the present invention, there is provided an ultrasonic diagnostic apparatus including: a transducer configured to perform interconversion between an acoustic wave and an electrical signal; and a transmitter for controlling the transducer so as to allow a plurality of plane waves to be transmitted through a plurality of sub-apertures.

The plurality of plane waves may be steered plane waves.

Furthermore, the plurality of plane waves may be transmitted sequentially.

In addition, the plurality of plane waves may be transmitted simultaneously.

Furthermore, apodization may be applied to at least one of the plurality of plane waves.

In addition, a window function may be applied to at least one of the plurality of plane waves as apodization.

Furthermore, at least one of the plurality of plane waves may include a chirp-type plane wave.

In addition, a first plane wave from among the plurality of plane waves may be an up-chirp type plane wave, and a second plane wave adjacent to the first plane wave may be a down-chirp type plane wave.

Furthermore, the transducer may receive echo signals corresponding to the plurality of plane waves from an object. The ultrasonic diagnostic apparatus may further include a receiver configured to receive electrical signals corresponding to the echo signals via the transducer.

Furthermore, the receiver may compress the electrical signals corresponding to the echo signals when the echo signals originate from chirp type plane waves.

In addition, the receiver may compress the electrical signals by using a signal of a chirp type opposite to that of the chirp-type plane waves.

Furthermore, the transducer may include: a first transducer configured to transmit a first plane wave through a first sub-aperture; and a second transducer spatially separated from the first transducer and configured to transmit a second plane wave through a second sub-aperture.

Furthermore, the first and second plane waves ray each have the same frequency band.

Furthermore, a steering angle for the first plane wave may be different from a steering angle for the second plane wave.

In addition, the steering angles for the first and second plane waves may be symmetric with respect to a direction in which an ultrasound wave travels.

According to another aspect of the present invention, there is provided an ultrasonic diagnostic method including: transmitting, through a plurality of sub-apertures, a plurality of plane waves to an object; and receiving, from the object, a plurality of echo signals respectively corresponding to the plurality of plane waves.

The plurality of plane waves may be transmitted simultaneously.

Furthermore, apodization may be applied to at least one of the plurality of plane waves.

Furthermore, at least one of the plurality of plane waves may include a chirp-type plane wave.

In addition, a first plane wave from among the plurality of plane waves may be an up-chirp type plane wave, and a second plane wave adjacent to the first plane wave may be a down-chirp type plane wave.

Advantageous Effects of the Invention

A clutter level may be reduced by using a plurality of plane waves transmitted through a plurality of sub-apertures.

By using a chirp-type plane wave, it is possible to prevent a drop in a frame rate of the plane wave while reducing a clutter level.

Furthermore, it is possible to reduce a fringing effect between plane waves by applying apodization to a plane wave.

MODE OF THE INVENTION

Figure 1:
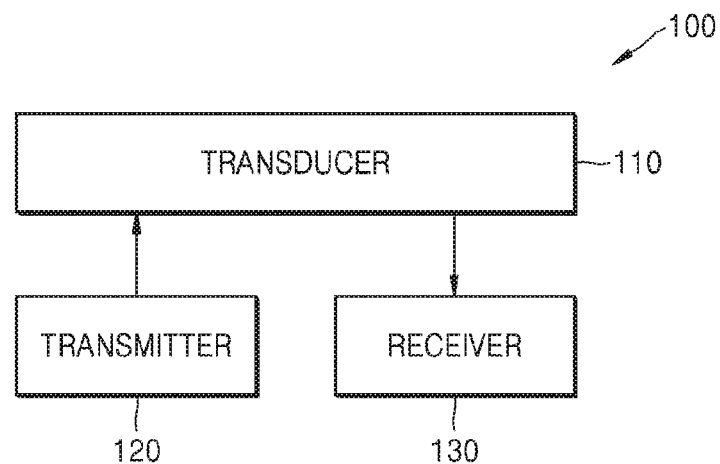
FIG. 1 is a block diagram of an ultrasonic diagnostic apparatus according to an exemplary embodiment.

Hereinafter, preferred exemplary embodiments of the present invention will be to described in detail with reference to the attached drawing in which the same or corresponding elements are denoted by the same reference numerals. Repeated descriptions of the same or corresponding elements are omitted.

Throughout the specification, an "object" may include a human or an animal, or a part of a human or animal. For example, the object may include an organ such as the liver, the heart, the womb, the brain, a breast, or the abdomen, or a blood vessel.

FIG. 1 is a block diagram of an ultrasonic diagnostic apparatus 100 according to an exemplary embodiment. Referring to FIG. 1, the ultrasonic diagnostic apparatus 100 may include a transducer 110, a transmitter 120, and a receiver 130. The ultrasonic diagnostic apparatus 100 may transmit an ultrasound wave in the form of a plane wave. The plane wave may be a steered plane wave. Furthermore, the plane wave may be a pulse type or chirp type plane wave, and apodization may be applied. Hereinafter, an ultrasound wave in the form of a plane wave may also be simply referred to as a plane wave.

The transducer 110 transmits ultrasound waves to an object and receives ultrasound echo signals reflected from the object. The transducer 110 may include a plurality of transducer elements for converting electrical signals into acoustic energy (or vice versa). The plurality of transducer elements may be arranged in a one-dimensional (1 D) or two-dimensional (2D) array.

The transducer 110 may be realized as a piezoelectric micromachined ultrasonic transducer (pMUT) that interconverts an ultrasound wave and an electrical signal due to a change in pressure caused by vibration, a capacitive micromachined ultrasonic transducer (cMUT) that interconverts an ultrasound wave and an electrical signal due to a change in capacitance, a magnetic micromachined ultrasonic transducer (mMUT) that interconvert an ultrasound wave and an electrical signal due to a change in magnetic field, and an optical ultrasonic detector that interconvert an ultrasound wave and an electrical signal due to a change in optical properties.

The transmitter 120 supplies a driving signal to the transducer 110. The transmitter 120 may control the transducer 110 so as to allow a plurality of plane waves to be transmitted through a plurality of sub-apertures. An aperture may be defined as a size of the transducer 110 for transmitting an ultrasound wave. The transmitter 120 according to an exemplary embodiment does not transmit a single wave by using all of the transducer elements included in the transducer 110 but may divide the transducer elements into several groups and control the transducer 110 so that each group of transducer elements transmits a wave. Thus, a size of each group of transducer elements for transmitting a wave may be defined as a sub-aperture. The transmitter 120 may control the transducer 110 to transmit a plurality of plane waves to an object through spatially separated sub-apertures. A method of transmitting a plurality of plane waves through a plurality of sub-apertures will be described in detail below.

The receiver 130 performs analog-to-digital conversion on a signal received from the transducer 110 to produce a digital signal and performs beamforming on the digital signal to form a focused reception signal. The receiver 130 may generate ultrasound data by using the focused reception signal. Since the transducer 110 transmits a plurality of plane waves through a plurality of sub-apertures and receives echo signals corresponding to the plurality of plane waves, the receiver 130 needs to add together the echo signals corresponding to the plurality of plane waves in order to acquire an image.

In addition, when the receiver 130 does not need to generate ultrasound data in real-time by using a signal received via the transducer 110, the receiver 130 may include only a storage for storing the signal received from the transducer 110.

While an ultrasound probe necessarily includes the transducer 110, at least some of the components in the transmitter 120 and the receiver 130 may be included in a device other than the ultrasound probe. For example, at least one of the transmitter 120 and the receiver 130 may be connected to the transducer 110 via a connector or network.

Figure 2:
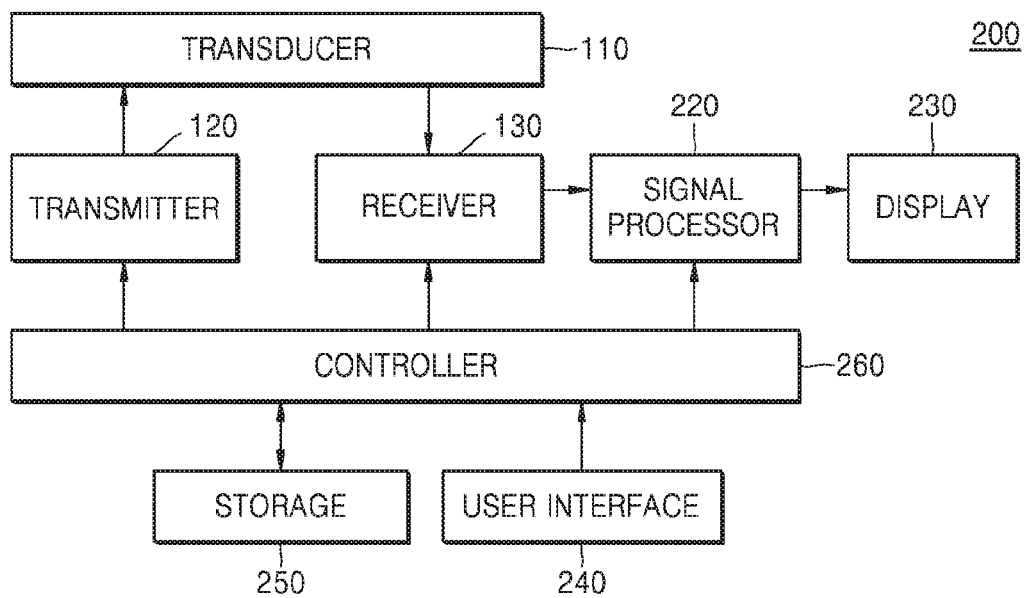
FIG. 2 is a block diagram of ultrasonic diagnostic apparatus according to another exemplary embodiment.

FIG. 2 is a block diagram of an ultrasonic diagnostic apparatus 200 according to another exemplary embodiment. Referring to FIG. 2, the ultrasonic diagnostic apparatus 200 may include, in addition to the transducer 110, the transmitter 120, and the receiver 130 shown in FIG. 1, a signal processor 220 for processing signals applied by the receiver 130 and generating an image, a display 230 for displaying the image, a user interface 240 for receiving a user command, a storage 250 for storing various types of information, and a controller 260 for controlling overall operations of the ultrasonic diagnostic apparatus 200.

The signal processor 220 may process ultrasound data generated by the receiver 130 and generate an ultrasound image. An ultrasound image may be at least one of a brightness (B) mode image representing a magnitude of an ultrasound echo signal to reflected from an object as brightness, a Doppler (0) mode image showing an image of a moving object in the form of a spectrum by using a Doppler effect, a motion (M) mode image representing movement of an object at a specific position over time, an elastic mode image visualizing a difference between responses when compression is or is not applied to an object as an image, and a color (C) mode image representing a velocity of a moving object in colors by using a Doppler effect. Since an ultrasound image is generated by using a method well known in the related art, a detailed description thereof will be omitted here. Accordingly, the ultrasound image according to an exemplary embodiment of the present invention may include images taken in all dimensions such as 1 D, 2D, three-dimension (3D), four-dimension (40), etc.

The display 230 displays information that is processed by the ultrasonic diagnostic apparatus 200. For example, the display 230 may display an ultrasound image generated by the signal processor 220 as well as a graphical user interface (GUI) for requesting a user input.

The display 230 may include at least one of a liquid crystal display (LCD), a thin film transistor-LCD (TFT- LCD), an organic light-emitting diode (OLED), a flexible display, a 3D display, and an electrophoretic display. The ultrasonic diagnostic apparatus 100 may include two or more displays 230 according to exemplary embodiments of the present invention.

The user interface 240 refers to a means via which a user inputs data for controlling the ultrasonic diagnostic apparatus 100. The user interface 240 may include a keypad, a mouse, a touch panel, and a track ball. The user interface 240 is not limited thereto, and may further include various other input elements such as a jog wheel and a jog switch.

The touch panel may detect both a real touch where a pointer actually touches a screen and a proximity touch where the pointer approaches the screen while being separated from the screen by less than a predetermined distance. In the present specification, the term 'pointer' means a tool for touching a particular portion on or near the touch panel. Examples of the pointer may include a stylus pen and a body part such as a finger.

Furthermore, the touch panel may be realized as a touch screen that forms a layer structure with the display 230. The touch screen may be implemented as various types such as capacitive overlay, resistive overlay, infrared beam, surface acoustic wave, to integral strain gauge, and piezoelectric touch screens. The touch screen is very useful because it functions as both the display 230 and the user interface 240.

Although not shown in FIG. 2, various sensors may be disposed within or near the touch panel so as to sense a touch. A tactile sensor is an example of the sensors designed for the touch panel to sense a touch. The tactile sensor is used to sense a touch of a particular object to a same or greater degree than the degree to which a human can sense the touch. The tactile sensor may detect various pieces of information including the toughness of a contact surface, the hardness of an object to be touched, and the temperature of a point to be touched.

A proximity sensor is another example of the sensors designed for the touch panel to sense a touch. The proximity sensor is a sensor that detects the presence of an object that is approaching or is located near a predetermined detection surface by using the force of an electromagnetic field or infrared light without any mechanical contact. Examples of the proximity sensor include a transmissive photoelectric sensor, a direct reflective photoelectric sensor, a mirror reflective photoelectric sensor, a high-frequency oscillation proximity sensor, a capacitive proximity sensor, a magnetic proximity sensor, and an infrared proximity sensor.

The storage 250 stores various types of information that are processed by the ultrasonic diagnostic apparatus 100. For example, the storage 250 may store medical data related to diagnosis of the object, such as images, and algorithms or programs that are executed in the ultrasonic diagnostic apparatus 100.

The storage 250 may include at least one storage medium from among a flash memory-type storage medium, a hard disk-type storage medium, a multimedia card micro-type storage medium, card-type memories (e.g., an SD card, an XD memory, and the like), a Random Access Memory (RAM), a Static Random Access Memory (SRAM), a Read-Only Memory (ROM), an Electrically Erasable Programmable ROM (EEPROM), a PROM, a magnetic memory, a magnetic disc, and an optical disc. Furthermore, the ultrasonic diagnostic apparatus 100 may utilize web storage or a cloud server that functions as the storage 250 online.

The controller 260 controls the overall operations of the ultrasonic diagnostic apparatus 100. In detail, the controller 260 may control operations of the ultrasonic diagnostic apparatus 100 of FIG. 2, the signal processor 220, and the display 230. For example, the controller 260 may control the signal processor 220 to generate an image by using a user command received via the user interface 240 or programs stored in the storage 250. The controller 260 may also control the image generated by the signal processor 220 to be displayed on the display 230.

As described above, the transducer 110 transmits and receives a wave such as a plane wave, and the transmitter 120 applies an electrical signal to the transducer 110 in is order for the transducer 110 to transmit a wave. When the transducer 110 receives a wave, the transducer 110 may apply an electrical signal corresponding to the received wave to the receiver 130. Thus, transmission of a plane wave by the ultrasonic diagnostic apparatus may mean that the transmitter 120 controls the transducer 110 to transmit the plane wave. Reception and processing of a plane wave by the ultrasonic diagnostic apparatus may mean that the transducer 110 receives an echo signal corresponding to a plane wave and the receiver 130 stores an electrical signal corresponding to the echo signal or generates ultrasound data based on the electrical signal. Hereinafter, for convenience of explanation, the transducer 110, the transmitter 120, and the receiver 130 are not individually named but simply referred to as the ultrasonic diagnostic apparatus.

An ultrasonic diagnostic apparatus according to an exemplary embodiment may transmit an ultrasound wave in the form of a plane wave. A plane wave may be generated using a time delay or phase delay of the transmitter 120. The use of a plane wave has advantages of generating an ultrasound image at a high frame rate and acquiring an ultrasound image of a wide area of an object. However, when an object is diagnosed using a plane wave, an echo signal may suffer a high clutter level since the plane wave has a high degree of scattering.

The ultrasonic diagnostic apparatus according to an exemplary embodiment may transmit a plurality of plane waves through a plurality of sub-apertures and receive echo signals corresponding to the plurality of plane waves, thereby generating an ultrasound image on a frame-by-frame basis. Thus, a clutter level may be reduced.

Figure 3:
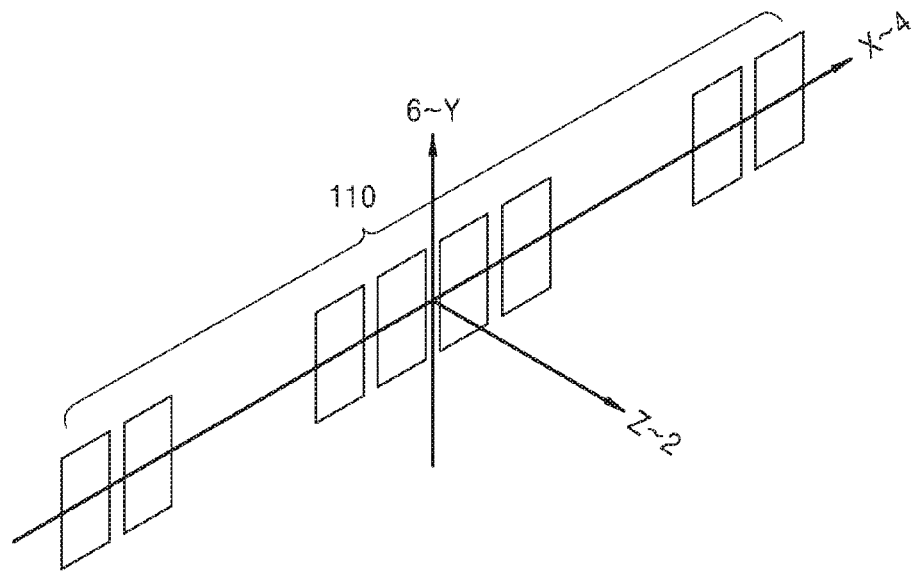
FIG. 3 is a reference diagram for explaining coordinates of an ultrasonic diagnostic apparatus.

Before describing a method of operating an ultrasonic diagnostic apparatus according to an exemplary embodiment, coordinates of the ultrasonic diagnostic apparatus are defined. FIG. 3 is a reference diagram for explaining coordinates of an ultrasonic diagnostic apparatus. As shown in FIG. 3, the resolution of an ultrasound image may be determined, based on a transducer element within the transducer 110, as to resolutions in an axial direction 2 defined as a direction in which a transmission wave travels, in a lateral direction 4 defined as a width direction of the transducer element, and in an elevation direction 6 defined as a height direction of the transducer element. The method of operating an ultrasonic diagnostic apparatus will be described below based on the coordinates.

Figure 4:
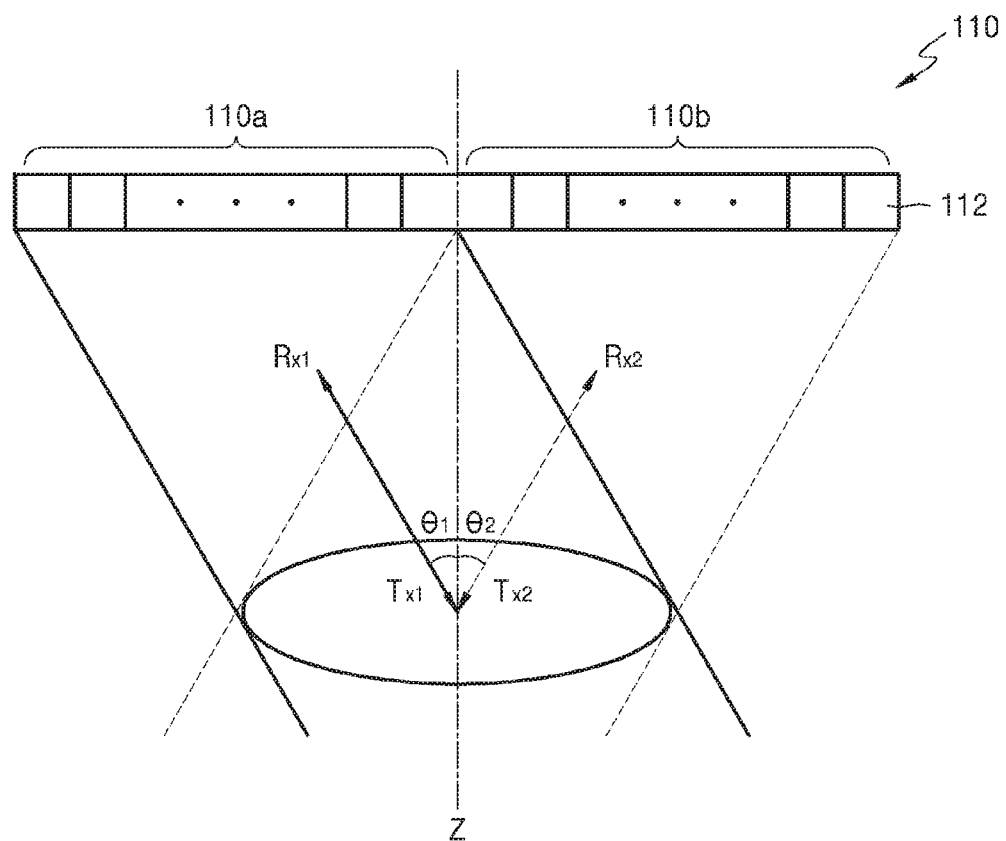
FIG. 4 is a reference diagram for explaining a method of transmitting a plurality of plane waves in a plurality of sub-apertures according to an exemplary embodiment.

FIG. 4 is a reference diagram for explaining a method of transmitting a plurality of plane waves in a plurality of sub-apertures according to an exemplary embodiment. As shown in FIG. 4, a transducer 110 of an ultrasonic diagnostic apparatus may include first and second transducers 110a and 110b spatially separated from each other. For example, the first and second transducers 110a and 110b may be arranged parallel to each other. Each of the first and second transducers 110a and 110b may include one or more transducer elements 112.

The transmitter 120 may control the first and second transducers 110a and 110b to transmit first and second plane waves Tx1 and Tx2, respectively. Sizes of the first and second transducers 110a and 110b for transmitting the first and second plane waves may be first and second sub-apertures, respectively. The transmitter 120 may control the first and second transducers 110a and 110b so as to allow the first and second plane waves Tx1 and Tx2 to be consecutively transmitted one by one. In this case, the first and second plane waves Tx1 and Tx2 may have the same frequency band but are not limited thereto.

For example, the transmitter 120 may control the first transducer 110a to transmit the first plane wave Tx1 at a first time, and after the first time has lapsed, control the second transducer 110b to transmit the second plane wave Tx2 at a second time. Furthermore, the first transducer 110a may receive an echo signal Rx1 generated in response to the first plane wave. The second transducer 110b may receive an echo signal Rx2 generated in response to the second plane wave. The receiver 130 may delay the timing of an electrical signal corresponding to an echo signal generated in response to the first plane wave and synthesize the electrical signal with an electrical signal corresponding to an echo signal generated in response to the second plane wave, thereby generating one piece of image data.

A steering angle θ1 for the first plane wave Tx1 may be different from a steering angle θ2 for the second plane wave Tx2. For example, the steering angles θ1 and θ2 for the first and second plane waves Tx1 and Tx2 may be symmetric with respect to an axial direction Z. Furthermore, the steering angle θ1 for the first plane wave Tx1 being transmitted by the first transducer 110a may be equal to a reception angle θ1 for the echo signal Rx1 generated in response to the first plane wave. The steering angle θ2 for the second plane wave Tx2 being transmitted by the second transducer 110b may be equal to a reception angle θ2 for the echo signal Rx2 generated in response to the second plane wave. As described above, when a plurality of plane waves are transmitted in a plurality of sub-apertures, a clutter level may be reduced by minimizing an aperture through which a plane wave is transmitted.

The following Table 1 shows a result of simulation for determining whether the clutter level was reduced. Parameters used in the simulation are summarized in Table 1 below.

TABLE 1

SIMULATION PARAMETERS

| PARAMETERS | Values |
|---|---|
| Center Frequency | 9 MHz |
| Sampling frequency | 72 MHz |
| Number of elements | 192 |
| Element height | 5 mm |
| Element pitch | 0.2 mm |
| Steering angle | ±20° |
| Number of TX | 33 |
| Target (axial) | 10 to 70 mm (20-mm interval) |
| Target (lateral) | −14 mm, 0 mm, 14 mm |

As shown in Table 1, a center frequency and a sampling frequency of a plane wave transmitted by the transducer 110 were 9 MHz and 72 MHz, respectively. The number of transducer elements in the transducer 110 was 192, and a transducer element had a height of 5 mm and a pitch of 0.2 mm. A steering angle was ±20°, and three targets were arranged at positions that were 50 mm away from the transducer 110 in an axial direction of the transducer element and were −14 mm, 0 mm, and 14 mm away from the transducer 110 in a lateral direction, respectively.

Figure 5A:
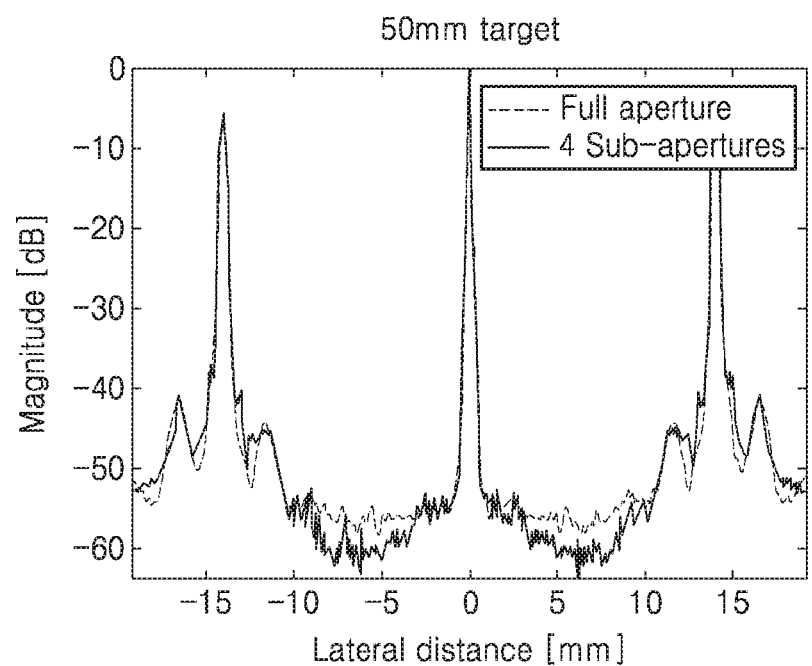
FIGS. 5A and 5B are reference diagrams for explaining a resolution of an ultrasound image acquired using a plane wave.
Figure 5B:
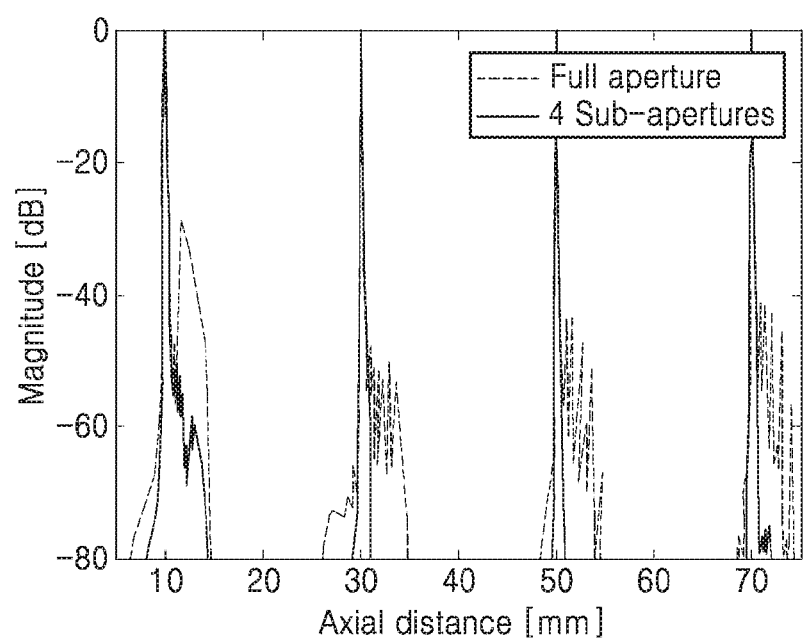

FIGS. 5A and 5B are reference diagrams for explaining the resolution of an ultrasound image acquired using a plane wave. A dashed line represents a magnitude of a signal received after transmission of a plane wave through one aperture while a solid line represents a magnitude of a signal received after transmission of four plane waves through four sub-apertures. As shown in FIGS. 5A and 5B, when plane waves are transmitted in a plurality of sub-apertures, magnitudes of echo signals corresponding to the plane waves are significantly reduced in a region where a target does not exist. It can be seen that an ultrasound image acquired by transmitting a plurality of plane waves through a plurality of sub-apertures contains less noise than an ultrasound image acquired by transmitting a plane wave through one aperture.

Transmitting and receiving a plurality of plane waves at different times may lower a frame rate. To prevent a drop in a frame rate, an ultrasonic diagnostic apparatus according to an exemplary embodiment may transmit a plurality of plane waves through a plurality of sub-apertures simultaneously. Even when the plurality of sub-apertures are physically separated, the plurality of plane waves may interfere with one another.

According to an exemplary embodiment, to reduce interference between a plurality of plane waves, the transmitter 120 of the ultrasonic diagnostic apparatus may control the transducer 110 so as to allow a plurality of chirp-type plane waves to be simultaneously transmitted. By transmitting the plurality of plane waves at the same to time, it is possible to maintain the same frame rate as that achieved by transmitting one plane wave.

For example, the transmitter 120 may control the transducer 110 so that the first transducer 110a of the transducer 110 shown in FIG. 3 may transmit a first plane wave Tx1 of an up-chirp type and the second transducer 110b may transmit a second plane wave Tx2 of a down-chirp type. The first and second plane waves Tx1 and Tx2 may have the same frequency band and be transmitted at the same time. Since a plurality of plane waves are transmitted and received at the same time, the same frame rate may be maintained. Furthermore, since the first and second plane waves Tx1 and Tx2 are of opposite chirp types, it is possible to reduce the crosstalk between the plurality of first and second plane waves.

Furthermore, the receiver 130 may compress an echo signal received via the transducer 110. Since the transducer 110 receives a plurality of chirp-type plane waves simultaneously, the receiver 130 may compress a signal received from the transducer 110 according to the directional characteristics of an echo signal. The compression may be pulse compression.

For example, if a received echo signal is of an up-chirp type, the receiver 130 may compress the received echo signal by using a down-chirp signal. If the received echo signal is of a down-chirp type, the receiver 130 may compress the received echo signal by using an up-chirp signal. In detail, the receiver 130 may compress an echo signal corresponding to a first plane wave, which is received via a first transducer 110, by using a down-chirp signal. The receiver 130 may compress an echo signal corresponding to a second plane wave, which is received via a second transducer 110, by using an up-chirp signal. As described above, when the receiver 130 compresses an echo signal by using an opposite type of chirp signal, a level of a signal output from the receiver 130 may be lowered, and accordingly, the time duration taken to generate a frame image may be reduced. However, exemplary embodiments are not limited thereto, and the receiver 130 may compress an echo signal by using the same type of chirp signal.

Furthermore, the ultrasonic diagnostic apparatus may generate a chirp-type plane wave combined with a window function. If the window function is combined with a chirp signal as described above, a sidelobe level of a compressed signal created by the receiver 130 may be reduced. For example, the window function may be a Hanning is) window, but is not limited thereto. Some examples of the window function may be a Blackman window, a cosine window, a Gaussian window, etc.

Figure 6A:
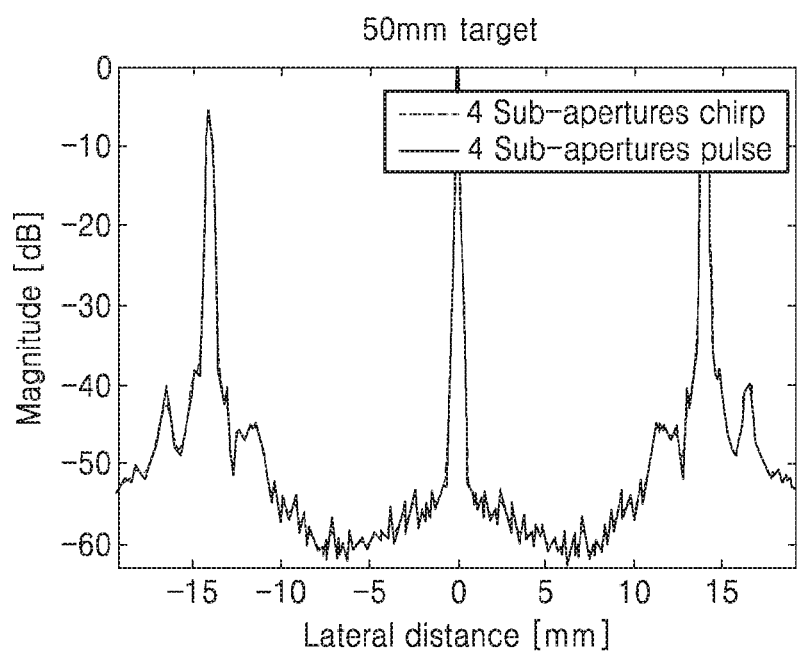
FIGS. 6A and 6B are reference diagrams for explaining an ultrasound image acquired using a chirp signal.
Figure 6B:
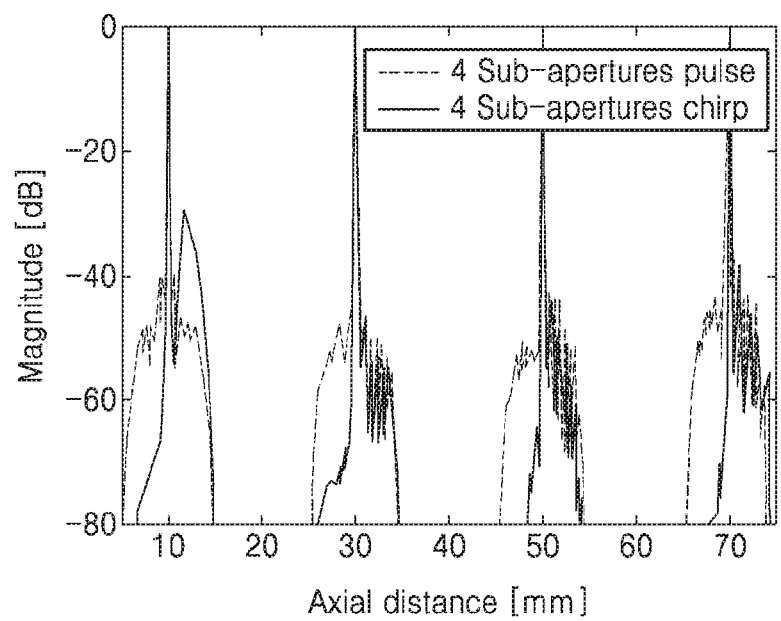

FIGS. 6A and 6B are reference diagrams for explaining an ultrasound image acquired using a chirp signal. A dashed line represents a magnitude of a signal received after transmission of pulse-type plane waves through four sub-apertures while a solid line represents a magnitude of a signal received after transmission of chirp-type plane waves through the four sub-apertures. As shown in FIGS. 6A and 6B, the use of a chirp-type plane wave may reduce a clutter level by about 8 decibels (dB) compared to the use of a pulse-type plane wave.

When adjacent plane waves are perpendicular to each other, the crosstalk between the adjacent plane waves may not occur. However, when adjacent plane waves are not perpendicular to each other, the crosstalk may still be present in an axial direction. Thus, the transmitter 120 may apply apodization to at least one of first and second plane waves Tx1 and Tx2, thereby reducing a fringing effect between the plane waves. A Hanning window may be used as an apodization function, but exemplary embodiments are not limited thereto. Another window function such as a rectangular window may also be used as an apodization function.

Figure 7A:
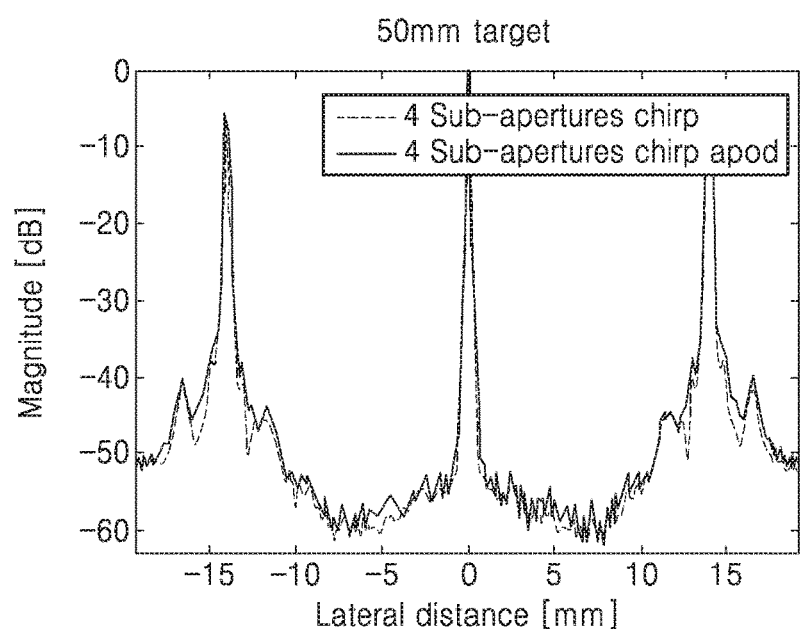
FIGS. 7A and 7B are reference diagrams for explaining an ultrasound image acquired by applying apodization.
Figure 7B:
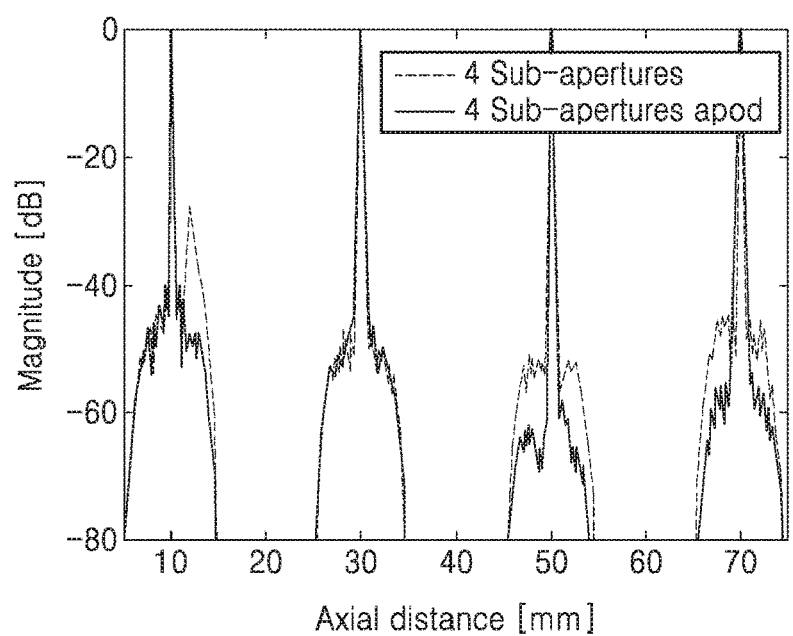

FIGS. 7A and 7B are reference diagrams for explaining an ultrasound image acquired by applying apodization. A dashed line represents a magnitude of a signal received after transmission of chirp-type plane waves through four sub-apertures while a solid line represents a magnitude of a signal received after transmission of chirp-type plane waves, to which apodization is applied, through the four sub-apertures. As shown in FIGS. 7A and 7B, the use of a chirp-type plane wave to which apodization is applied may further reduce a clutter level compared to the use of a chirp-type plane wave to which apodization is not applied.

While FIGS. 7A and 7B show that apodization is applied to a chirp-type plane wave, exemplary embodiments are not limited thereto. Apodization may be applied to another type of plane wave.

Figure 8:
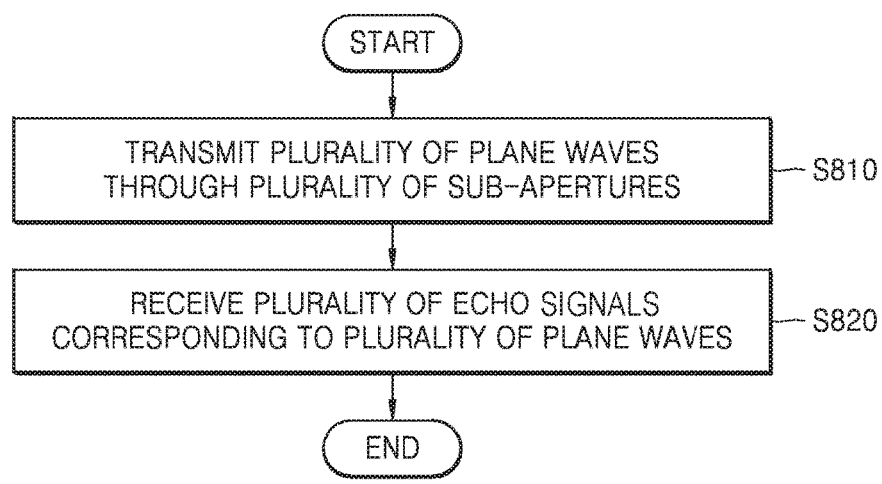
FIG. 8 is a flowchart of an ultrasonic diagnostic method according to an exemplary embodiment.

FIG. 8 is a flowchart of an ultrasonic diagnostic method according to an exemplary embodiment.

Referring to FIG. 8, an ultrasonic diagnostic apparatus may transmit a plurality of plane waves through a plurality of sub-apertures (S810) and receive a plurality of echo to signals respectively corresponding to the plurality of plane waves from an object (S820).

The plurality of plane waves may be transmitted sequentially or simultaneously. When the plurality of plane waves are transmitted sequentially, a frame rate may be lowered. However, when the plurality of plane waves are transmitted simultaneously, interference between plane waves occurs. To reduce the interference between plane waves, at least one of the plurality of plane waves may be of a chirp type. For example, a first plane wave from among the plurality of plane waves may be an up-chirp type plane wave while a second plane wave contiguous to the first plane wave may be a down-chirp type plane wave.

Furthermore, apodization may be applied to at least one of the plurality of plane waves. By applying apodization to a plane wave, a clutter level may be further reduced.

In addition, the method of transmitting and receiving a plane wave and the signal processing method described above may be applied to the ultrasonic diagnostic method.

While it has been described above that a transducer element for transmitting or receiving a first plane wave is different from a transducer element for transmitting or receiving a second plane wave when an ultrasonic diagnostic apparatus according to an exemplary embodiment transmits a plurality of plane waves, this is only for convenience of explanation, and exemplary embodiments are not limited thereto. One transducer element may transmit some of the first and second plane waves in order for the ultrasonic diagnostic apparatus to transmit a plurality of spatially separated plane waves.

Although the above-described ultrasound waves are plane waves, exemplary embodiments are not limited thereto, and the ultrasound waves may be defocused ultrasound waves. That is, a transducer may transmit a defocused ultrasound wave by transmitting an ultrasound wave by varying a phase.

Many embodiments other than the above-described exemplary embodiments may be present in the claims of the present invention. As the present disclosure allows for various changes and numerous embodiments, exemplary embodiments are illustrated in the drawings and described in detail in the description. However, this is not intended to limit the present disclosure to a particular mode of practice, and it is to be appreciated that the present disclosure encompasses all changes, equivalents, and substitutes that do not depart from the spirit and technical scope thereof.

The invention claimed is:

1. An ultrasonic diagnostic apparatus comprising:
   a transducer comprising:
      first transducer elements configured to transmit an up-chirped plane wave and receive a first echo signal corresponding to the up-chirped plane wave, from an object, and
      second transducer elements spatially separated from the first transducer elements and configured to transmit a down-chirped plane wave and receive a second echo signal corresponding to the down-chirped plane wave, from the object;
   a receiver configured to receive first electrical signals corresponding to the first echo signal from the first transducer elements and second electrical signals corresponding to the second echo signal from the second transducer elements, and compress the first electrical signals by using a down-chirped signal and the second electrical signals by using an up-chirped signal; and
   a signal processor configured to generate an ultrasound image using the compressed first electrical signals and the compressed second electrical signals; and
   a controller configured to control the first transducer elements to transmit the up-chirped plane wave at a first steering angle and the second transducer elements to transmit the down-chirped plane wave at a second steering angle different from the first steering angle, the first steering angle and the second steering angle being symmetric with respect to an axial direction of the transducer, such that the up-chirped plane wave and the down-chirped plane wave are transmitted to a same portion of the object.

2. The ultrasonic diagnostic apparatus of claim 1, wherein the controller is further configured to control the first transducer elements to transmit the up-chirped plane wave and the second transducer elements to transmit the down-chirped plane wave sequentially.

3. The ultrasonic diagnostic apparatus of claim 1, wherein the controller is further configured to control the first transducer elements to transmit the up-chirped plane wave and the second transducer elements to transmit the down-chirped plane wave simultaneously.

4. The ultrasonic diagnostic apparatus of claim 1, wherein each of the up-chirped plane wave and the down-chirped plane wave has a same frequency band.

5. An ultrasonic diagnostic method comprising:
   transmitting, through first transducer elements, an up-chirped plane wave to an object at a first steering angle, and transmitting, through second transducer elements spatially separated from the first transducer elements, a down-chirped plane wave to the object at a second steering angle different from the first steering angle, the first steering angle and the second steering angle being symmetric with respect to an axial direction of a transducer comprising the first transducer elements and the second transducer elements, such that the up-chirped plane wave and the down-chirped plane wave are transmitted to a same portion of the object;
   receiving, from the object, a first echo signal corresponding to the up-chirped plane wave and a second echo signal corresponding to the down-chirped plane wave, by the first transducer elements and the second transducer elements, respectively,
   receiving, by a receiver, first electrical signals corresponding to the first echo signal from the first transducer elements and second electrical signals corresponding to the second echo signal from the second transducer elements;
   compressing the first electrical signals by using a down-chirped signal and the second electrical signals by using an up-chirped signal; and
   generating an ultrasound image using the compressed first electrical signals and the compressed second electrical signals.

6. The ultrasonic diagnostic method of claim 5, wherein the up-chirped plane wave and the down-chirped plane wave are transmitted simultaneously.

7. The ultrasonic diagnostic method of claim 5, wherein an apodization is applied to at least one among the up-chirped plane wave and the down-chirped plane wave.

* * * * *